United States Patent
Lichtenstein

(10) Patent No.: US 9,615,760 B2
(45) Date of Patent: Apr. 11, 2017

(54) MULTIPLE BIPOLAR SAMPLING

(71) Applicant: BIOSENSE WEBSTER (ISRAEL), LTD., Yokneam (IL)

(72) Inventor: Yoav Lichtenstein, Raanana (IL)

(73) Assignee: BIOSENSE WEBSTER (ISRAEL), LTD. (IL)

(*) Notice: Subject to any disclaimer, the term of this patent is extended or adjusted under 35 U.S.C. 154(b) by 655 days.

(21) Appl. No.: 13/919,229

(22) Filed: Jun. 17, 2013

(65) Prior Publication Data
US 2014/0371563 A1    Dec. 18, 2014

(51) Int. Cl.
| | | |
|---|---|---|
| A61B 5/04 | (2006.01) | |
| A61B 5/042 | (2006.01) | |
| A61B 5/0428 | (2006.01) | |
| A61B 18/04 | (2006.01) | |
| A61B 5/00 | (2006.01) | |
| A61N 1/05 | (2006.01) | |

(52) U.S. Cl.
CPC ........ *A61B 5/0422* (2013.01); *A61B 5/04288* (2013.01); *A61B 5/7225* (2013.01); *A61B 5/6852* (2013.01); *A61B 2560/0481* (2013.01); *A61B 2562/0209* (2013.01); *A61B 2562/043* (2013.01); *A61N 1/05* (2013.01)

(58) Field of Classification Search
CPC ...... A61B 18/1492; A61B 2018/00875; A61B 2018/00839; A61B 2018/00351; A61B 18/1233; A61B 2018/1253; A61B 2018/126; H01L 27/14692; A61N 1/05; A61N 1/08
USPC ........ 600/372–374, 377, 381, 393, 508–509; 606/32–35, 48–50
See application file for complete search history.

(56) References Cited

U.S. PATENT DOCUMENTS

| | | | | |
|---|---|---|---|---|
| 5,073,733 A | * | 12/1991 | Tanno | H03K 5/135 327/261 |
| 5,514,129 A | | 5/1996 | Smith | |
| 5,722,401 A | * | 3/1998 | Pietroski | A61B 5/0422 600/374 |
| 5,991,650 A | * | 11/1999 | Swanson | A61B 5/0422 374/E1.005 |
| 6,001,095 A | | 12/1999 | De la Rama et al. | |

(Continued)

FOREIGN PATENT DOCUMENTS

| | | |
|---|---|---|
| WO | 99/12607 A1 | 3/1999 |
| WO | 2006/029090 A2 | 3/2006 |

OTHER PUBLICATIONS

Office Action for co-pending EP Application No. 14172581.2, mailed Oct. 6, 2015; 5 pages.

(Continued)

*Primary Examiner* — Joseph Stoklosa
*Assistant Examiner* — Brian M Antiskay

(57) ABSTRACT

Apparatus, which consists of a plurality of modules. Each of the modules has: an insulating frame, a pair of electrodes fixed to the frame at respective locations that are spaced apart, and circuitry configured to receive signals from the pair of electrodes and in response output a differential signal. The apparatus further consists of an insertion tube having distal and proximal ends and containing the plurality of modules in locations spaced longitudinally in proximity to the distal end. There is cabling running through the tube that is connected to convey differential signals from the modules to the proximal end.

8 Claims, 8 Drawing Sheets

(56) References Cited

U.S. PATENT DOCUMENTS

| | | | |
|---|---|---|---|
| 6,088,610 A | 7/2000 | Littmann et al. | |
| 6,097,976 A * | 8/2000 | Yang | A61L 29/085 600/373 |
| 6,241,727 B1 | 6/2001 | Tu et al. | |
| 6,550,321 B1 | 4/2003 | Patey et al. | |
| 8,095,206 B2 * | 1/2012 | Ghanem | A61N 1/3704 600/509 |
| 8,147,486 B2 * | 4/2012 | Honour | A61B 5/0422 606/41 |
| 8,226,648 B2 | 7/2012 | Paul et al. | |
| 2002/0161306 A1 * | 10/2002 | Govari | A61B 5/0422 600/509 |
| 2006/0058588 A1 * | 3/2006 | Zdeblick | A61B 5/0422 600/300 |
| 2009/0062790 A1 | 3/2009 | Malchano et al. | |
| 2010/0079158 A1 | 4/2010 | Bar-Tal et al. | |
| 2012/0203100 A1 * | 8/2012 | Weiss | A61B 5/0422 600/421 |
| 2012/0253340 A1 * | 10/2012 | Stevenson | A61N 1/05 606/33 |
| 2013/0006084 A1 * | 1/2013 | Harlev | A61B 5/0538 600/374 |
| 2013/0165917 A1 * | 6/2013 | Mathur | A61B 18/18 606/33 |
| 2013/0245413 A1 * | 9/2013 | Dabney | A61N 1/08 600/373 |
| 2014/0081114 A1 * | 3/2014 | Shachar | A61B 5/6858 600/378 |

OTHER PUBLICATIONS

European Search Report for European Patent Application No. 14172581.2, mailed on Sep. 14, 2014; 7 pages.

* cited by examiner

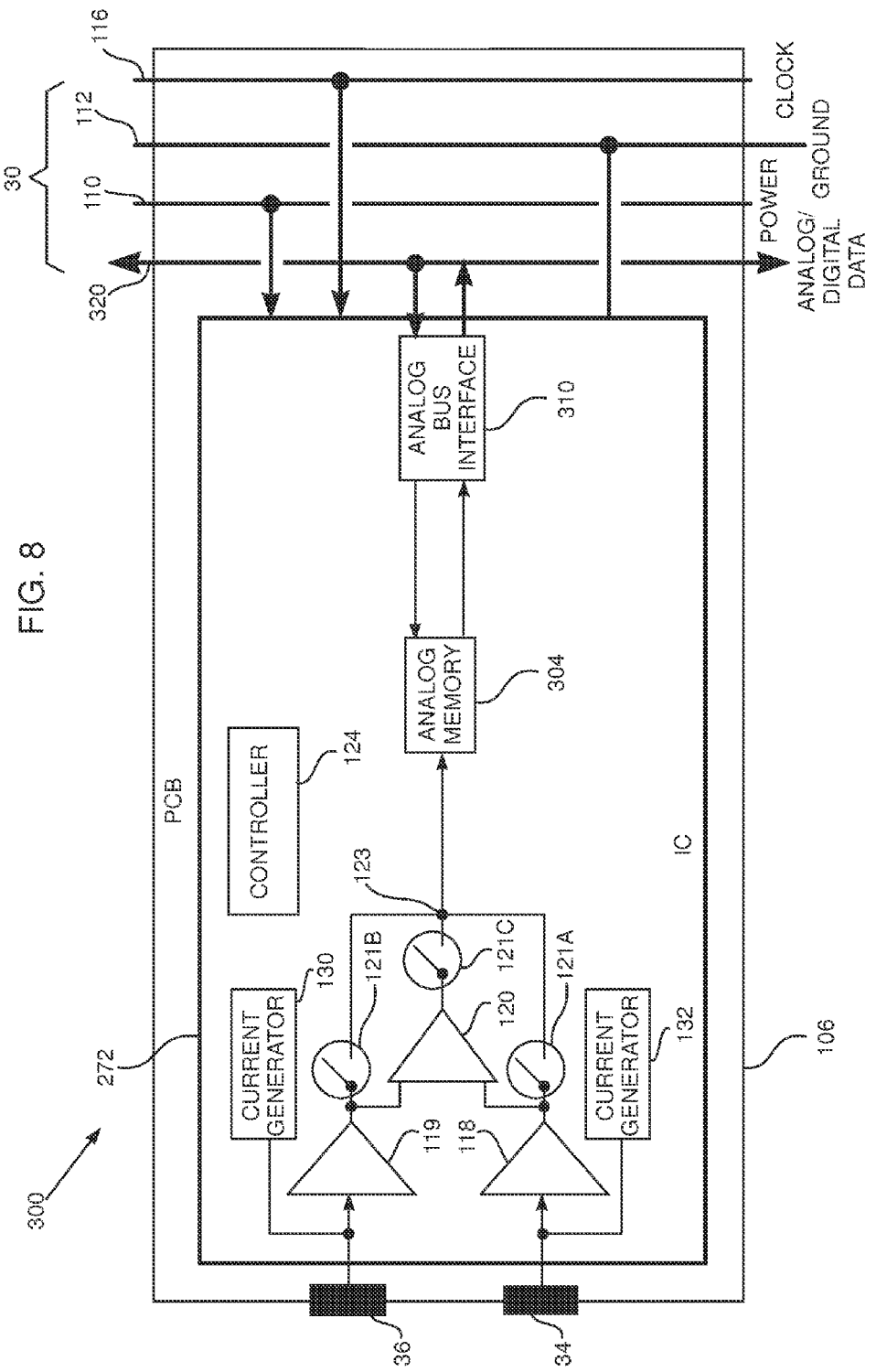

US 9,615,760 B2

MULTIPLE BIPOLAR SAMPLING

FIELD OF THE INVENTION

The present invention relates generally to signal transmission using conductors, and specifically to transmitting multiple signals over a minimal number of conductors.

BACKGROUND OF THE INVENTION

In a surgical procedure, a relatively large number of measurements on a patient may need to be made simultaneously, and the measurements may need to be transferred from the patient to a relatively distant console where the measurements may be analyzed and displayed. The problems of transfer may be exacerbated by limited access to the patient. In minimally invasive medical surgery for example, the size of the access to a patient undergoing the surgery may be extremely limited, so that catheters or tools used for the surgery need to have diameters of the order of millimeters. Minimizing the number of conductors used to transfer the measurements enables the diameters of the catheters or tools to be reduced, with corresponding benefit to the patient.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides apparatus, including:

a plurality of modules, each module including:

an insulating frame;

a pair of electrodes fixed to the frame at respective locations that are spaced apart; and circuitry configured to receive signals from the pair of electrodes and in response output a differential signal;

an insertion tube having distal and proximal ends and containing the plurality of modules in locations spaced longitudinally in proximity to the distal end; and cabling running through the tube and connected to convey differential signals from the modules to the proximal end.

The insulating frame typically consists of a printed circuit board (PCB), and the circuitry may be mounted on the PCB.

In a disclosed embodiment the cabling includes a data line and a ground line configured to convey the differential signals. The data line may be configured to convey clock signals and power in addition to the differential signals.

In a further disclosed embodiment the circuitry includes a current generator configured to inject current via one of the pair of electrodes into a patient wherein the distal end is inserted, and the apparatus further includes a processor configured to measure different currents received at a surface of the patient in response to the injected current, and to determine a location of the one of the pair of electrodes in response to the measured different currents.

In a yet further disclosed embodiment the insertion tube is incorporated within a catheter inserted into a heart of a patient, and the differential signals are generated in response to electropotentials acquired by the pair of electrodes due to contact with the heart.

In an alternative embodiment the cabling is connected to the plurality of modules so as to maintain the plurality of modules in the longitudinally spaced locations.

In a further alternative embodiment the circuitry is configured to receive signals from one of the pair of electrodes and in response to output a unipolar signal, and the cabling is configured to convey the unipolar signal to the proximal end.

In a yet further alternative embodiment the circuitry includes a memory configured to store the signals, and a controller, and the controller is configured to delay outputting data from the memory so as to reduce noise.

There is further provided, according to an embodiment of the present invention, a method, including:

providing an insertion tube having distal and proximal ends;

inserting into the tube a plurality of modules so that the modules are in locations in the tube spaced longitudinally in proximity to the distal end, each module including:

an insulating frame;

a pair of electrodes fixed to the frame at respective locations that are spaced apart; and circuitry configured to receive signals from the pair of electrodes and in response output a differential signal; and running cabling through the tube and connecting the cabling to convey differential signals from the modules to the proximal end.

The present disclosure will be more fully understood from the following detailed description of the embodiments thereof, taken together with the drawings, in which:

BRIEF DESCRIPTION OF THE DRAWINGS

FIG. 8 is a schematic block diagram illustrating elements of the module of FIG. 7, according to an embodiment of the present invention.

DETAILED DESCRIPTION OF EMBODIMENTS

Overview

Figure 1:
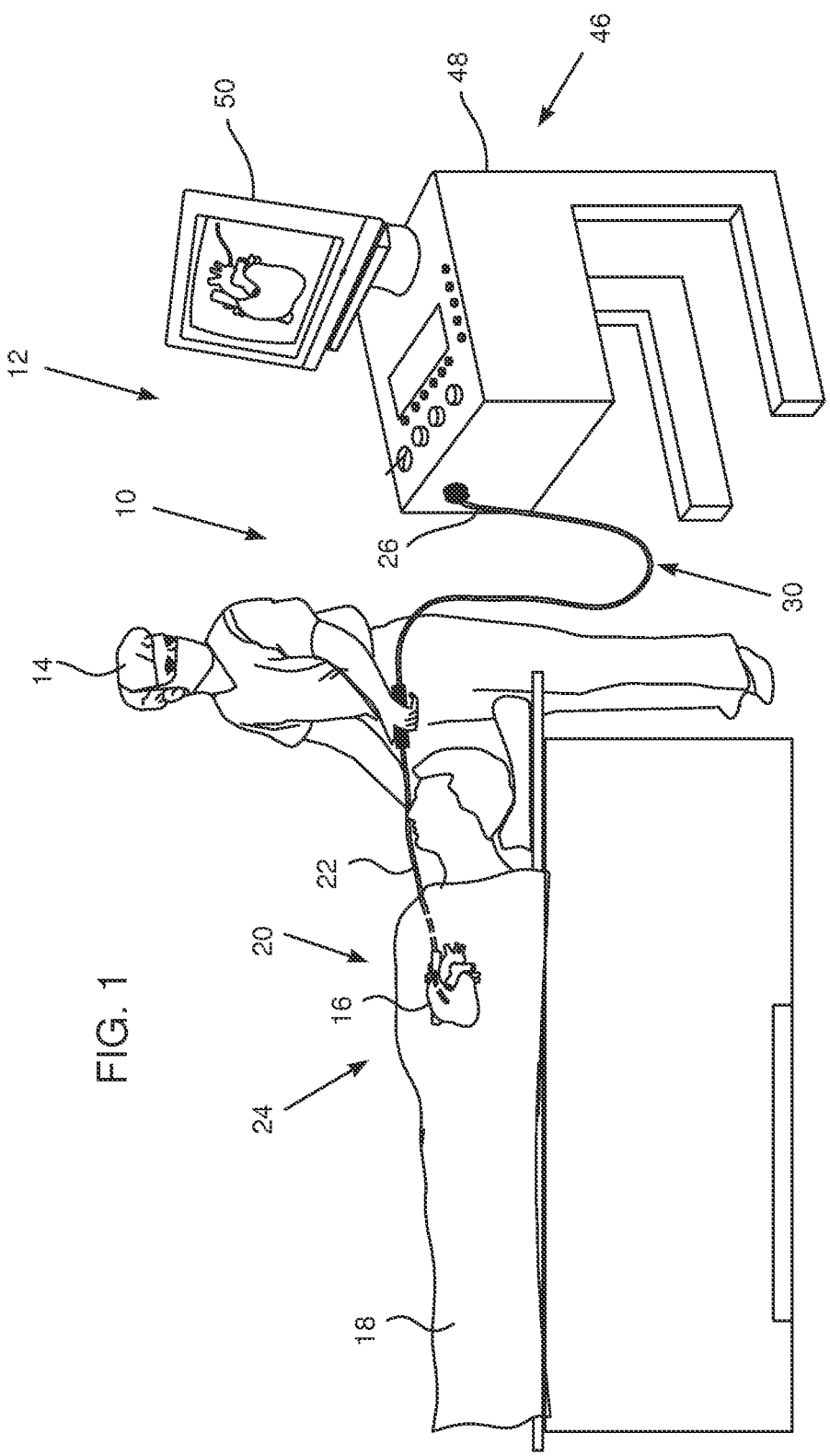
FIG. 1 is a schematic illustration of an invasive medical procedure using a multiple bipolar sampling system, according to an embodiment of the present invention.

An embodiment of the present invention provides a plurality of modules which may be inserted into an insertion tube, typically so that the plurality of modules are positioned at locations spaced longitudinally in proximity to a distal end of the tube. The tube has a proximal end, and typically forms part of a catheter. Each module has an insulating frame, typically a printed circuit board (PCB), to which a pair of electrodes are fixed, the frame acting to separate the pair of electrodes by a substantially unvarying distance. Each module also includes circuitry which is configured to receive signals, typically bipolar signals, from its pair of electrodes, and in response outputs a differential signal. Alternatively or additionally, the circuitry may be configured to receive unipolar signals from one or both of the electrodes. Except where otherwise stated, for simplicity the following description assumes that bipolar signals are received from the pair of electrodes of a given module.

If the tube is inserted into the heart of a patient, each pair of electrodes may be used to acquire the bipolar signals from electropotentials generated at locations where the electrodes contact the heart.

Cabling runs through the insertion tube between the distal and proximal ends of the tube, and the cabling is connected to the modules so as to convey the differential signals of the modules to the proximal end of the tube. Typically, a processor is connected to the proximal end, so as to receive the differential signals.

The cabling connecting the modules typically comprises four conductors, although in some embodiments only two conductors are used for the cabling. However, the number of modules in the plurality is virtually unlimited, and may typically be five or more. Thus, in the case of a catheter inserted into the heart, a large number of bipolar signals may be acquired by the catheter using four or even fewer conductors traversing the catheter.

System Description

In the following description, like elements in the drawings are identified by like numerals, and the like elements are differentiated as necessary by appending a letter to the identifying numeral.

Figure 2:
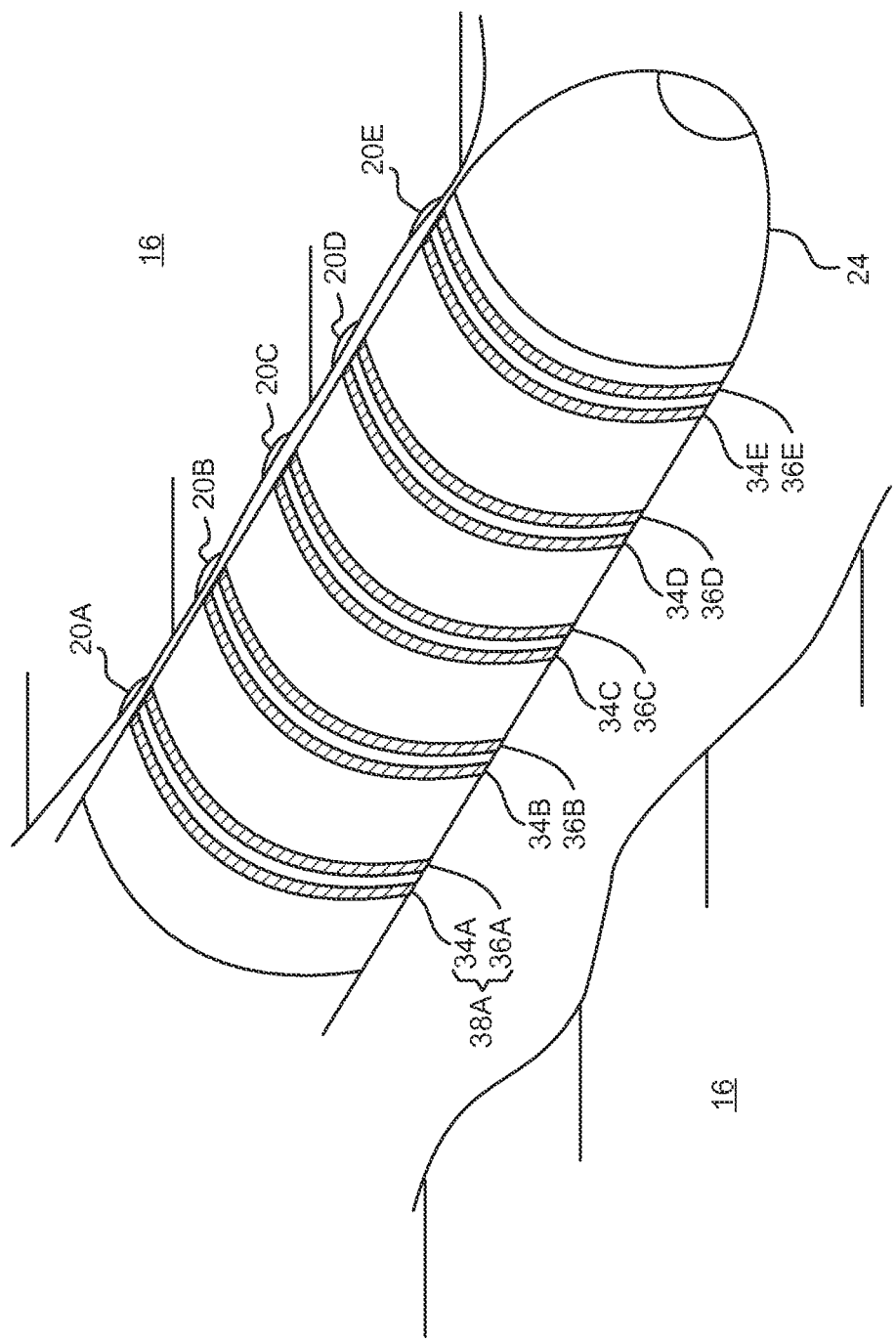
FIG. 2 is a schematic illustration of an external view of a distal end of an insertion tube used in the system, according to an embodiment of the present invention.

FIG. 1 is a schematic illustration of an invasive medical procedure using a multiple bipolar sampling system 10, and FIG. 2 is a schematic illustration of an external view of a distal end of an insertion tube used in the system, according to embodiments of the present invention. By way of example, system 10 is assumed to be incorporated into an apparatus 12 used for an invasive medical procedure, performed by a medical professional 14, on a myocardium 16 of the heart of a human patient 18. The medical procedure comprises measurements of bipolar electropotentials of the heart at multiple locations 20, locations 20A, 20B, . . . , of the myocardium. In order to perform the measurements, professional 14 inserts a catheter 22, herein also referred to as insertion tube 22, into the patient, so that a distal end 24 of the insertion tube enters the heart of the patient. Insertion tube 22 has a proximal end 26.

As is illustrated in FIG. 2, distal end 24 comprises generally similar pairs of cylindrical electrodes 34, 36, e.g. electrodes 34A, 36A; 34B, 36B; 34C, 36C; . . . . In the disclosure, for simplicity a pair of electrodes 34, 36 may also be referred to as electrodes 38, so that, for example, electrodes 34A, 36A may also be referred to as electrodes 38A. Electrodes 38 acquire electropotentials of regions with which they are in contact, and in the following description electrodes 38A, 38B, 38C, . . . are assumed to be respectively in contact with locations 20A, 20B, 20C, . . . of the myocardium.

System 10 is controlled by a system processor 46, which is located in an operating console 48 of apparatus 12. During the procedure, processor 46 typically tracks a location and an orientation of distal end 24 of the catheter, using any method known in the art. For example, processor 46 may use a magnetic tracking method, wherein magnetic transmitters external to patient 18 generate signals in coils positioned in the distal end. The Carto® system produced by Biosense Webster, of Diamond Bar, Calif., uses such a tracking method. By tracking the location and orientation of distal end 24, and from a knowledge of the physical dimensions of the distal end and its electrodes 38, processor 46 is able to estimate numerical values for locations 20A, 20B, 20C, . . . in contact with the electrodes. An alternative method for tracking distal end 24, using currents injected into electrodes 38, is described below.

As explained in more detail below, signals derived from electropotentials acquired by electrodes 38, due to electrode contact with the heart, are transferred back via cabling 30 in catheter 22 to processor 46. The processor may analyze the received signals, and may present results of the analysis on a screen 50 attached to the console. The results derived from the analysis typically include maps of electrical characteristics of the heart such as local activation times, numerical displays, and/or graphs of the electropotentials vs. time.

Figure 3:
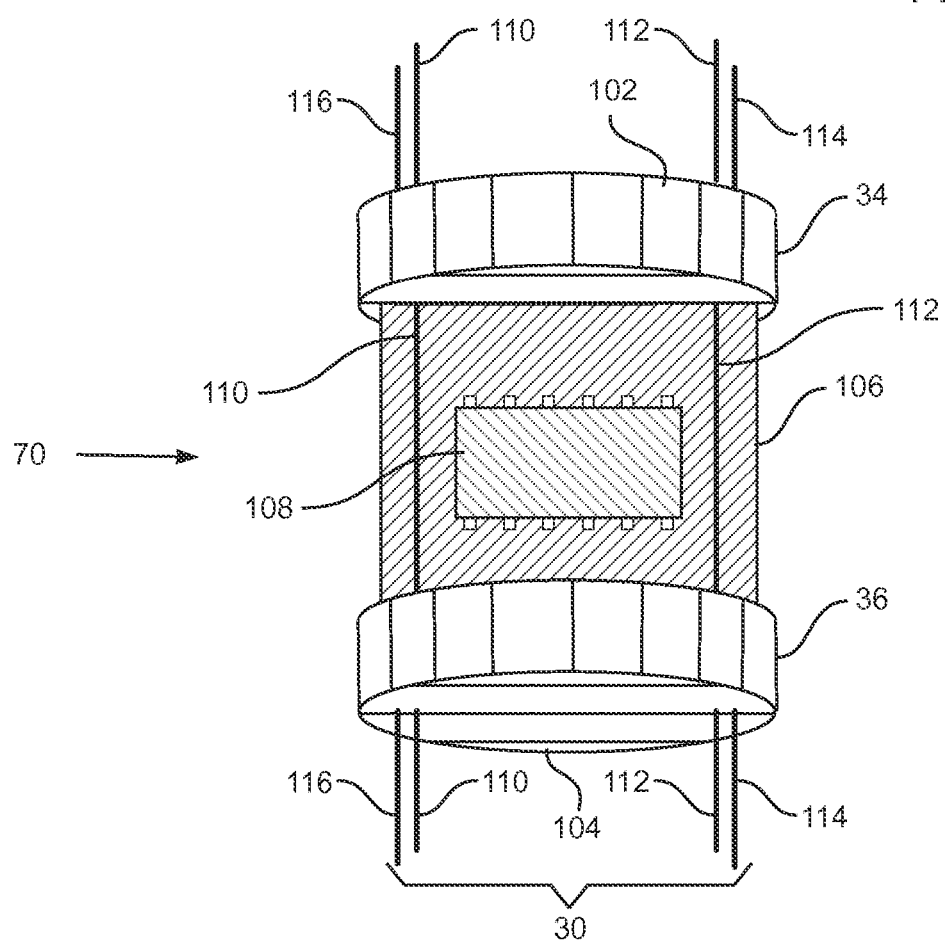
FIG. 3 is a schematic diagram illustrating a bipolar sampling module used by the system, according to an embodiment of the present invention.
Figure 4:
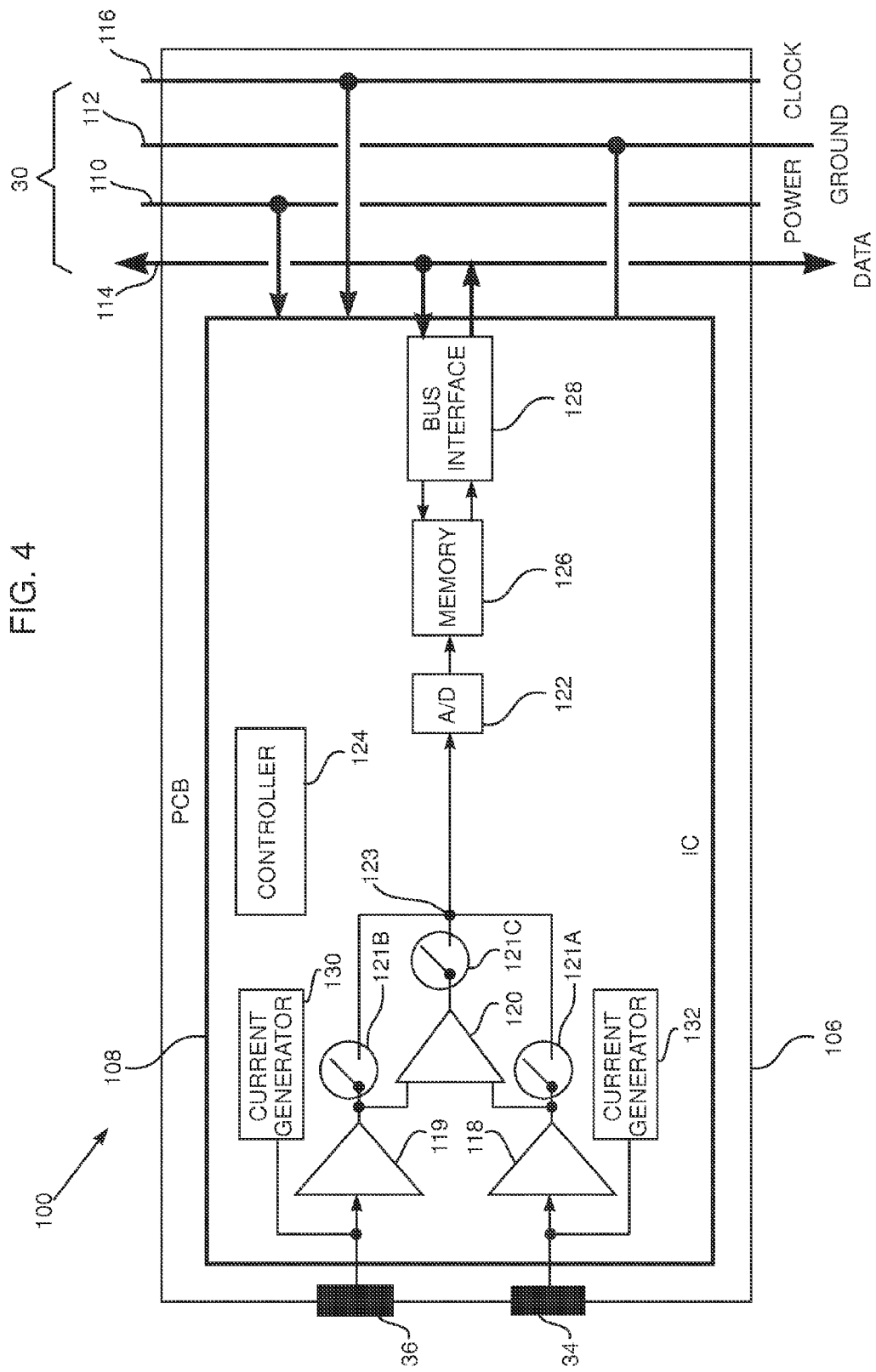
FIG. 4 is a schematic block diagram illustrating elements of the sampling module, according to an embodiment of the present invention.

FIG. 3 is a schematic diagram illustrating a bipolar sampling module 70 used by system 10, and FIG. 4 is a schematic block diagram 100 illustrating elements of the sampling module, according to embodiments of the present invention. Bipolar sampling module 70 comprises two generally similar insulating discs 102 and 104, and cylindrical electrodes 34, 36 are formed upon the outer cylindrical faces of the discs. Discs 102 and 104 are connected together by an insulated frame, herein assumed to comprise a plane printed circuit board (PCB) and referred to herein as PCB 106. Circuitry 108, herein assumed to comprise an integrated circuit (IC) and also referred to herein as IC 108, is mounted on PCB 106. A power conductor 110, and a return, ground, conductor 112 traverse component 70, and are used to power IC 108. A third conductor 114 transfers data to and from the integrated circuit, the third conductor acting as a data bus line and thus is also herein termed data line 114. A fourth conductor 116 transmits a clock signal to circuit 108, and is also herein termed clock line 116. Data line 114 and clock line 116 both traverse module 70. As is explained in more detail below, conductors 110, 112, 114, and 116 are included in cabling 30.

Electrodes 34, 36, and conductors 110, 112, 114, and 116 are all connected to IC 108. For simplicity, the connections are not shown in FIG. 3, but are shown in FIG. 4.

IC 108 comprises two buffer amplifiers 118, 119, which are respectively connected to receive inputs from electrodes 34 and 36. The outputs from the buffer amplifiers are connected as inputs to a differential amplifier 120, which may also be configured as a buffer and a low-pass filter. IC 108 also comprises on/off switches 121A, 121B, and 121C, which are respectively connected to the outputs of buffer amplifiers 118, 119, and differential amplifier 120. Switches 121A, 121B, and 121C are referred to generically as switches 121.

Switches 121 and other elements of IC 108 are under local control of a local controller 124 which receives clock signals from clock line 116 or from data line 114. By closing or opening switches 121, controller 124 is able to operate module 70 in a bipolar mode or in a unipolar mode. Thus, if switches 121A and 121B are open, and switch 121C is closed, signals from electrodes 34 and 36 are transferred to the input of differential amplifier 12, which outputs its differential signal to a junction 123. In this configuration module 70 operates in a bipolar mode.

If switch 121A is closed and switches 121B and 121C are open, signals from electrode 34 transfer, via buffer amplifier 118, to junction 123. If switch 121B is closed and switches 121A and 121C are open, signals from electrode 36 transfer via buffer amplifier 119 to junction 123. In these two configurations module 70 operates in a unipolar mode, in which ground line 112 is typically connected to a Wilson central terminal (WCT), or to a potential level equivalent to the WCT.

Signals from junction 123 are input directly to an analog-to-digital (A/D) converter 122, and controller 124 stores data generated by A/D 122 in a local memory 126. Controller 124 is able to transfer data from memory 126 to data line 114 via a bus interface 128; the controller is also able to transfer data into module 70, such as parameters for operating amplifier 120, via the bus interface. In the bipolar mode processor 46 (FIG. 1) is able to use the data generated by A/D 122, and transferred via data line 114, to acquire the bipolar signal generated between electrodes 34 and 36. In the unipolar mode, the processor may acquire the unipolar signals from electrodes 34 or 36.

It will be understood that by time multiplexing different states of switches 121, embodiments of the present invention are able to provide to junction 123, substantially simultaneously, a bipolar signal as well as two unipolar signals from electrodes 34 and 36. Other methods for substantially simultaneously providing a bipolar signal and two unipolar signals to junction 123, using the elements of IC 108, mutatis mutandis, will be apparent to those having ordinary skill in the art, and all such methods are included in the scope of the present invention.

In some embodiments, IC 108 incorporates local current generators 130, 132, which are respectively connected to electrodes 36 and 34. Controller 124 and/or processor 46 are configured to operate the current generators to inject currents from the electrodes into patient 18, and to measure currents, herein termed skin-currents, received in response to the current injection at electrodes (not shown in FIG. 1) located on the skin of the patient. Methods for locating an electrode of a catheter within a patient, by measuring values of different currents travelling between the catheter electrode and electrodes on the surface of the patient, are known in the art.

For example, U.S. Patent Application 2010/0079158 to Bar-Tal et al., whose disclosure is incorporated herein by reference, describes a tracking system for an investigation tool within a patient, using measurements of investigation tool currents. Those having ordinary skill will be able to use the disclosure of U.S. Patent Application 2010/0079158, mutatis mutandis, to determine locations of electrodes 34 and/or 36, using measured values of skin-currents generated in response to currents injected by generators 130 and/or 132.

Figure 5:
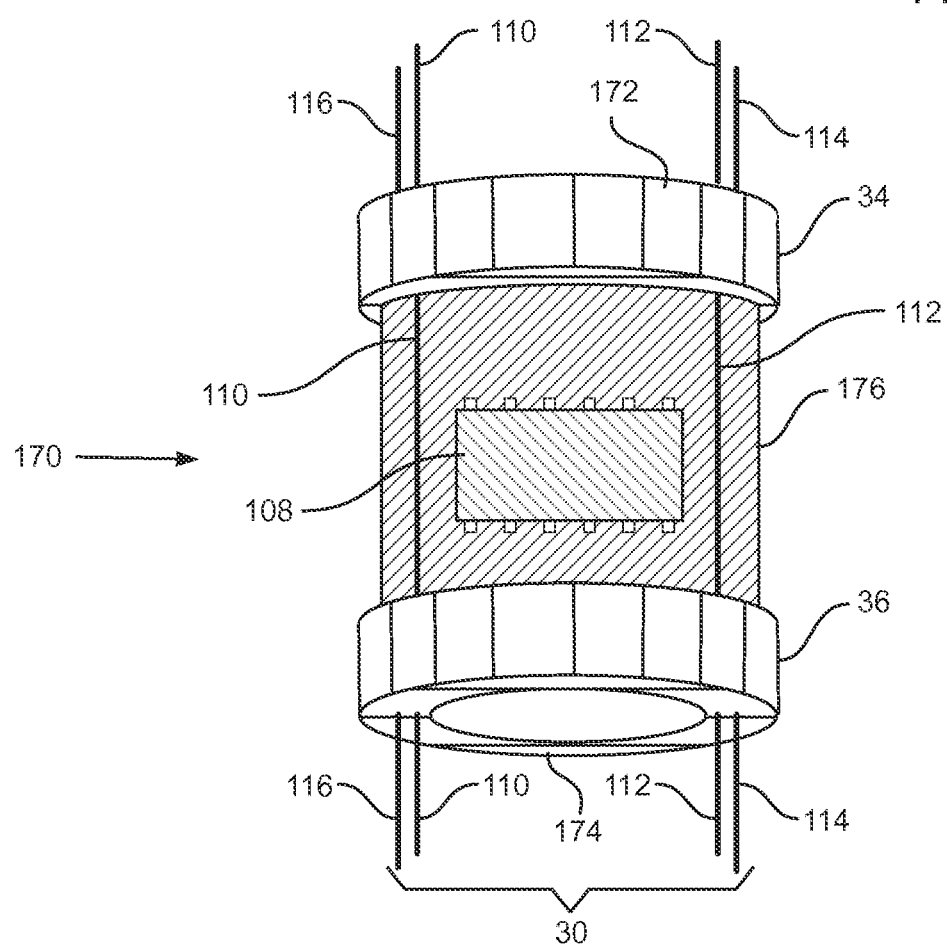
FIG. 5 is a schematic diagram illustrating a bipolar sampling module used by the system, according to an alternative embodiment of the present invention.

FIG. 5 is a schematic diagram illustrating a bipolar sampling module 170 used by system 10, according to an alternative embodiment of the present invention. Apart from the differences described below, the operation of module 170 is generally similar to that of module 70 (FIGS. 3 and 4), and elements indicated by the same reference numerals in both modules 70 and 170 are generally similar in construction and in operation. In module 170, cylindrical electrodes 34, 36 are formed on the outer cylindrical surfaces of insulating rings 172 and 174, the rings replacing insulating discs 102 and 104 of module 70. As for module 70 rings 172 and 174 are connected together by an insulating frame, which is herein assumed to comprise a curved PCB 176. In some embodiments PCB 176 may comprise a flexible PCB. The configuration of module 170 enables elements, such as tubing and/or cabling, to be threaded through the central vacant regions of rings 172 and 174.

Figure 6:
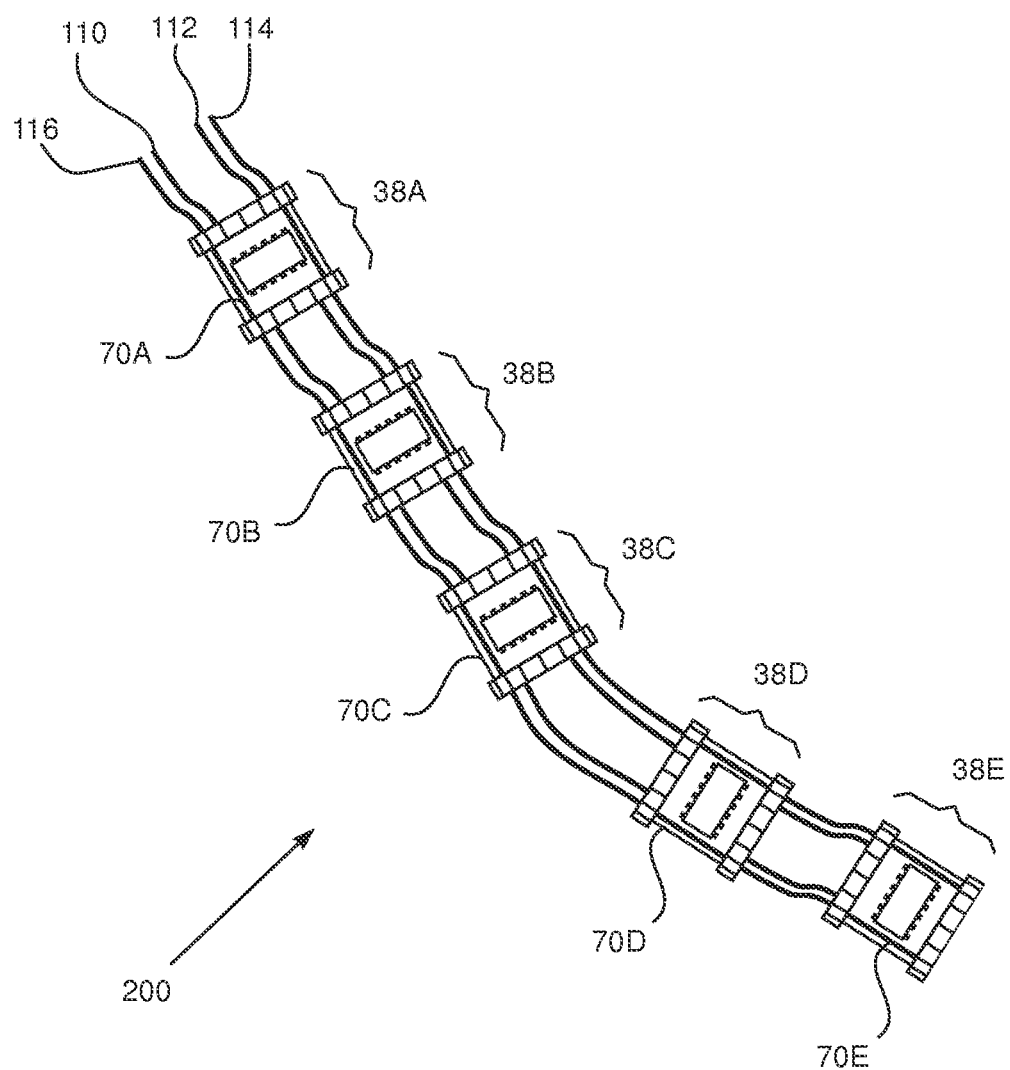
FIG. 6 is a schematic diagram illustrating multiple sampling modules connected together in a serial configuration, according to an embodiment of the present invention.

FIG. 6 is a schematic diagram illustrating multiple sampling modules 70 connected together in a serial configuration 200, according to an embodiment of the present invention. Those having ordinary skill in the art will be able to adapt the following description if at least some modules 170 are connected together in place of modules 70 in a serial configuration. By way of example, in serial configuration 200 there are assumed to be five modules 70, modules 70A, 70B, 70C, 70D, and 70E, having respective electrode pairs 38A, 38B, 38C, 38D, and 38E. Modules 70A, 70B, 70C, 70D, and 70E are connected together in the serial configuration, which may be installed in distal end 24 (FIG. 2), so that the modules are spaced longitudinally within, or in proximity to, the distal end. Typically, in order to install the serial configuration within the distal end, "windows" are formed in an outer covering of the distal end. The windows are configured to align with electrode pairs 38A, 38B, 38C, 38D, and 38E, enabling the electrode pairs to acquire signals from locations 20A, 20B, 20C, . . . of the myocardium (FIG. 2).

In order to connect the modules together, all connected modules have common conductor lines 110, 112, 114, and 116, which traverse catheter 22, and which are used to physically join the modules in their serial configuration, as well as to maintain the modules in their longitudinally spaced locations in the distal end. Conductor lines 110, 112, 114, and 116 are also used to convey signals and power between the modules themselves, as well as between the modules and processor 46 (FIG. 1).

Thus, using data line 114, processor 46 is able to receive values of the bipolar signals generated by each electrode pair 38, or of unipolar signals generated by a selected electrode 34 or a selected electrode 36. Typically, a unique address is assigned to each module 70 so that, by addressing a given module, the processor receives digital values of the bipolar or unipolar signal generated at that module. The transfer of data from the different modules of configuration 200 to processor 46 is typically implemented using time-multiplexing.

Figure 7:
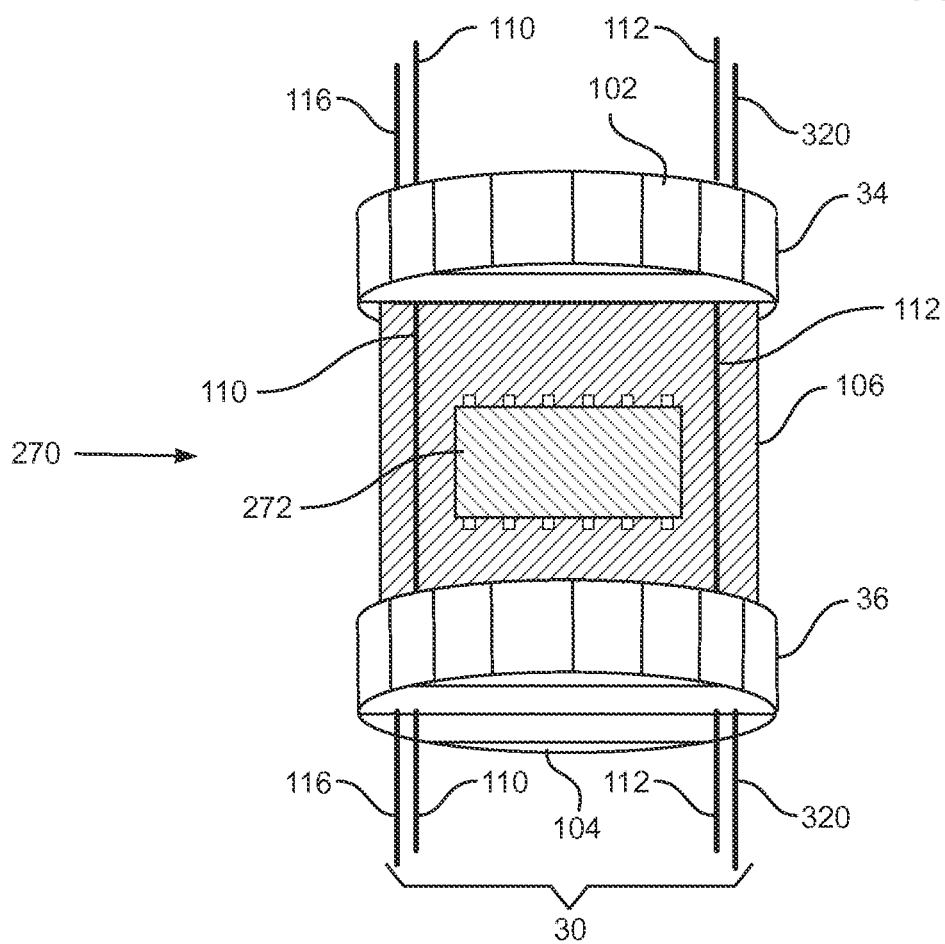
FIG. 7 is a schematic diagram illustrating a bipolar sampling module used by the system, according to a further alternative embodiment of the present invention.

FIG. 7 is a schematic diagram illustrating a bipolar sampling module 270 used by system 10, and FIG. 8 is a schematic block diagram 300 illustrating elements of module 270, according to alternative embodiments of the present invention. In contrast to module 70, which comprises IC 108, module 270 comprises an IC 272. Block diagram 300 illustrates the operation of IC 272. Apart from the differences described below, the operations of module 270 and IC 272 are generally similar to that of module 70 and IC 108 (FIGS. 3 and 4), and elements indicated by the same reference numerals in both modules 70 and 270 and IC 108 and IC 272 are generally similar in construction and in operation.

In IC 272, instead of signals from junction 123 being directly transferred to A/D 122, the signals are input to an analog memory 304. In some embodiments, analog memory 304 operates on a "bucket-brigade" principle, storing values of signals received from junction 123 in an analog format. Typically, controller 124 may operate IC 272 in a delayed manner, using analog memory 304 to store a set of signals acquired over a pre-determined period of time, such as 1 second, before transmitting the signals via data line 114. Delaying the transmission of the signals until a set of signals has been acquired may allow controller 124 to reduce the noise of the acquired signals. It will be understood that such a delay may also be implemented for module 70 using IC 108 (FIGS. 3 and 4).

In module 270 neither A/D 122 nor memory 126 are present. Rather, analog data from analog memory 304 is transferred directly to an analog bus interface 310 (which replaces bus interface 128 described above), and from interface 310 to a data bus 320. Data bus 320 is configured to transmit analog data, from modules such as module 270, as well as digital data, from modules such as module 70.

A plurality of modules 270 may be arranged in a series configuration substantially similar to configuration 200, described above (FIG. 6). Alternatively, a mixture of modules 70 and modules 270 may be arranged in such a configuration. Returning to the description of series configuration 200, modules 70 are connected together by cabling 30, comprising four conductors 110, 112, 114, and 116, which are respectively used as power, ground, data, and clock lines. Ground line 112 acts as a return line for the power transferred via power line 110. Typically, ground line 112 may be connected at the system processor side to a low impedance driver with an output potential equivalent to a Wilson central terminal (WCT) of patient 18; in addition, for embodiments having local current generators 130 and/or 132, ground line 112 acts as a return line for the generators. Thus, four conductors may be used to power and acquire signals from a large, virtually unlimited, number of modules; typically the number of modules in configuration 200 may be five or more.

In some embodiments, rather than having three separate conductors 110, 114, and 116, a single conductor is used for the power, data, and clock lines, using a multiplexing process controlled by processor 46. For example, the clock and data signals may be time multiplexed to give a combined signal, and the power, since it is DC, may be overlaid on the combined signal. Other methods for transferring power, data, and clock signals on a single conductor will be apparent to those having ordinary skill in the art, and all such methods are assumed to be within the scope of the present invention.

Consequently, in series configurations such as those exemplified by configuration 200, only two conductors may be used to connect the modules of the configuration, rather than the four conductors described above. In this case there is no loss of functionality for the configuration, and there is no reduction in the large, virtually unlimited, numbers of modules, that may be included in the configuration.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:
1. Apparatus, comprising:
a plurality of modules, each module comprising:
an insulating frame, the insulating frame comprising a printed circuit board (PCB);
a pair of insulating discs connected to the insulating frame, the pair of insulating discs including a first insulating disc connected at a distal end of the insulating frame and a second insulating disc connected at a proximal end of the insulating frame, the insulating frame longitudinally separating the first insulating disc from the second insulating disc;
a pair of electrodes including a first electrode formed on an outer surface of the first insulating disc and a second electrode formed on an outer surface of the second insulation disc, the pair of electrodes being configured to measure electropotential signals from a myocardium; and
circuitry mounted on the PCB and configured to receive the electropotential_signals from the pair of electrodes and in response output a differential signal;
an insertion tube having distal and proximal ends and containing the plurality of modules in locations spaced longitudinally in proximity to the distal end; and
cabling running through the tube and connected to convey differential signals from the modules to the proximal end.

2. The apparatus according to claim 1, wherein the cabling comprises a data line and a ground line configured to convey the differential signals.

3. The apparatus according to claim 2, wherein the data line is configured to convey clock signals and power in addition to the differential signals.

4. The apparatus according to claim 1, wherein the circuitry comprises a current generator configured to inject current via one of the pair of electrodes into a patient wherein the distal end is inserted, the apparatus further comprising a processor configured to measure different currents received at a surface of the patient in response to the injected current, and to determine a location of the one of the pair of electrodes in response to the measured different currents.

5. The apparatus according to claim 1, wherein the insertion tube is comprised in a catheter inserted into a heart of a patient, and wherein the differential signals are generated in response to electropotentials acquired by the pair of electrodes due to contact with the heart.

6. The apparatus according to claim 1, wherein the cabling is connected to the plurality of modules so as to maintain the plurality of modules in the longitudinally spaced locations.

7. The apparatus according to claim 1, wherein the circuitry is configured to receive signals from one of the pair of electrodes and in response to output a unipolar signal, and wherein the cabling is configured to convey the unipolar signal to the proximal end.

8. The apparatus according to claim 1, wherein the circuitry comprises a memory configured to store the signals, and a controller, and wherein the controller is configured to delay outputting data from the memory so as to reduce noise.

* * * * *